US00PP08705P

United States Patent [19]

McRae

[11] Patent Number: Plant 8,705

[45] Date of Patent: Apr. 26, 1994

[54] ASIATIC LILY CULTIVAR NAMED PORTLANDIA

[75] Inventor: Edward A. McRae, Woodland, Wash.

[73] Assignee: Cebeco Lilies, Inc., Aurora, Oreg.

[21] Appl. No.: 901,612

[22] Filed: Jun. 16, 1992

[51] Int. Cl.[5] ..... A01H 5/00

[52] U.S. Cl. ..... Plt./87.4

[58] Field of Search ..... Plt. 87.4

[56]

References Cited

Plt. 6003 9/1987 McRae ..... Plt./68

*Primary Examiner*—James R. Feyrer
*Assistant Examiner*—Erich Veitenheimer
*Attorney, Agent, or Firm*—Raymond B. Cranfill

[57] ABSTRACT

A new and distinctive asiatic hybrid lily plant is disclosed. The plant has medium-sized flowers, particularly distinguished by their brilliant orange-red coloration, borne profusely in upright racemes and by a vigorous, upright growth habit.

1 Drawing Sheet

BACKGROUND OF THE NEW PLANT

My new lily plant was selected from hybrid offspring of a cross of the lily variety Tribute (U.S. Plant Pat. No. 6,003) with pollen from an unnamed and unpatented plant selected from a group of lilies maintained for breeding purposes at a nursery in Sandy, Oreg. The present plant was selected from among the hybrid offspring of the aforementioned cross because of its brilliant orange-red coloration, profuse production of flowers and its vigorous growth habit. The selected seedling was propagated at Sandy, Oreg. by scaling and was carried through several successive generations in order to demonstrate that its novel and desirable characteristics would hold true from generation to generation. Such cultivation amply demonstrated the fixed and constant nature of these characteristics. Propagation of this new plant can be and has been carried out by conventional asexual methods, particularly scaling and tissue culture.

DESCRIPTION OF THE DRAWING

This new variety of lily is illustrated by the accompanying photographic drawing, which shows a face view of a mature blossom in true color rendition as close to that specified herein as can be obtained with conventional photographic procedures.

DESCRIPTION OF THE NEW PLANT

The following is a detailed description of my new lily plant as observed at Aurora, Oreg., with color designations according to the R.H.S. Colour Chart published by the Royal Horticultural Society of London, England.

THE PLANT

Genealogy and Classification

Origin: Seedling derived from a hybrid cross.
Parentage:
*Seed parent.*—Lilium Tribute, U.S. Plant Pat. No. 6,003.
*Pollen parent.*—Variety No. A 86-82, unpatented, selected from a collection of lily varieties maintained for breeding at Sandy, Oreg.
Classification:
*Botanic.*—Division 1-A, Upright Asiatic Lily Hybrid, UPR Asiatic Hybrid Lily.

*Commercial.*—Hybrid Lily Clone.

Habit

Form: Single erect stem.
Height: About 100 cm, field grown from bulbs ranging 25 cm in circumference, under adequate light levels.
Branching: None.
Growth: Vigorous and upright with good strength.

LEAVES

Quantity: Abundant.
Size: About 12 to 15 cm long and about 1 to 1.3 cm wide with entire margins.
Shape: Linear.
Texture: Leathery.
Color:
*Upper side.*—dark green.
*Lower side.*—light green.

Bulbs

Size: More or less 25 cm in circumference for commercial use.
Color: White.

Inflorescence

Habit: Racemose, averaging 12 flowers throughout the length of the raceme on plants derived from 12–14 cm bulbs, each flower upright in habit on a pedicel diverging about 45° from the vertical.
Length: About 30–38 cm long and about 18 cm wide.
Character: Erect and strong.
Color: Yellow green (146-A).

The Bud

Shape: Ovoid and elongate with an obtuse apex.
Size: About 2 cm in diameter and about 6.5 cm long just prior to flowering.
Opening rate: Slow in response to light.
Color: Orange-red (30-B) just before opening.

The Flower

Periodicity: Once per year, mid season.
Flower size: Medium, about 11–13 cm in diameter and about 6 cm deep.
Flower shape: Cup-shaped upon opening, but becoming progressively flattened as maturity is reached.
Tepal number: Six.
Tepal arrangement: Imbricate.

Tepal shape: Elliptical, acute at apex with entire margins.
Tepal texture: Leathery, glossy.
Tepal color:
*Outer tepals.*—Body — Orange-Red (32-A). Base — Orange-Red (32-B). Reverse Side — Orange-Red (30-C).
*Inner tepals.*—Body — Orange-Red (30-A). Base — Orange-Red (32-B). Reverse side — Orange-Red (30-B).
Tepal spotting: Tepals are marked with small, oblong red-purple (60-A) spots from the tepal base extending outward for about a third of the tepal length.
Nectaries: One per tepal, papillose, 2 cm long.
Papillae: Minute, few, on veins on each side of nectaries, white.
Pedicel length: About 5–7 cm.
Pedicel color: Yellow Green (146-A).
Pedicel habit: Stout, sharply ascending upward at an 45° from the horizontal.
Discoloration: Tepals fade in color (30-B) as flower ages.
Fragrance: None.
Duration: Long lasting, generally one to two weeks when cut, longer when left on the plant.
Disease resistance: Resistant to fusarium wilt and tolerant of viral infections as observed at Aurora, Oreg.

Stamens

Number: Six.
Arrangement: Lilium-type.
Anther size: About 1.2 cm.
Anther color: (31-B).
Filament length: About 4 cm.
Filament color: (20-B).
Pollen color: (33-A).

Pistils

Number: One.
Style length: About 3.75 cm.
Style color: (31-A).
Stigma color: (34-A).

The Fruit

Fertility: Fruit produces fertile seed.
Shape: Ovoid.
Color: Brown at maturity.

I claim:

1. The new and distinctive variety of asiatic hybrid lily substantially as shown and described herein, characterized in particular by a tepals having a bright orange-red coloration, medium-sized flowers produced profusely in racemes, and a vigorous growth habit.

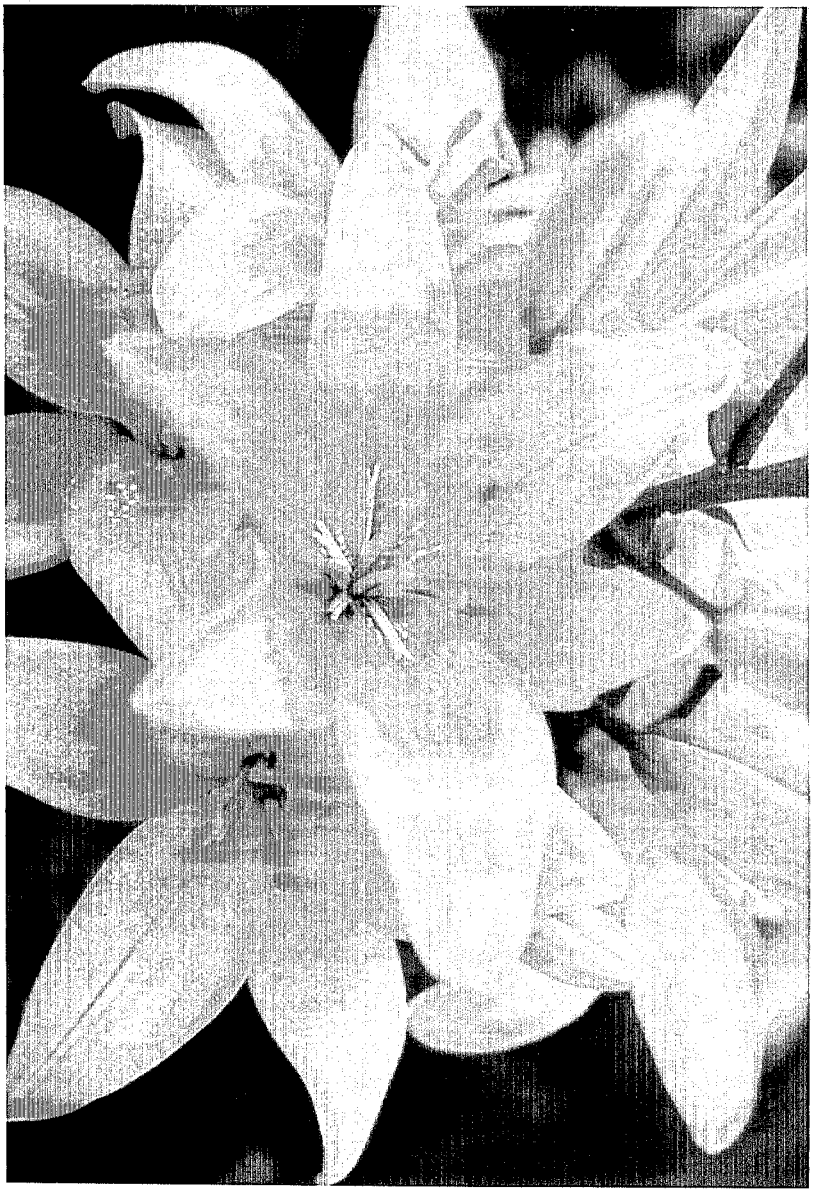

* * * * *